US005694693A

United States Patent [19]
Hutchins et al.

[11] Patent Number: 5,694,693
[45] Date of Patent: Dec. 9, 1997

[54] UNIVERSAL SAW BLADE HUB

[75] Inventors: Paul A. Hutchins, Charlottesville; John H. Pascaloff, Keswick, both of Va.

[73] Assignee: MicroAire Surgical Instruments, Inc., Charlottesville, Va.

[21] Appl. No.: 664,547

[22] Filed: Jun. 17, 1996

[51] Int. Cl.$^6$ .................................... A61B 17/14
[52] U.S. Cl. ................ 30/166.3; 606/176; 606/178; 30/355
[58] Field of Search .................. 30/355, 357, 342, 30/346; 606/82, 176, 177, 178; D24/146; 83/698.11, 835

[56] References Cited

U.S. PATENT DOCUMENTS

| | | |
|---|---|---|
| D. 343,247 | 1/1994 | Walen . |
| 3,943,934 | 3/1976 | Bent .................... 606/178 |
| 5,265,343 | 11/1993 | Pascaloff . |
| 5,306,285 | 4/1994 | Miller et al. . |
| 5,423,845 | 6/1995 | McDaniel .............. 606/176 |
| 5,489,285 | 2/1996 | Goris . |
| 5,496,316 | 3/1996 | Goris . |
| 5,507,763 | 4/1996 | Petersen et al. ........ 606/176 |

OTHER PUBLICATIONS

"SYNVASIVE® Technology, Inc., Precision Replacement Blade Catalog", p. 33.

*Primary Examiner*—Hwei-Siu Payer
*Attorney, Agent, or Firm*—Whitham, Curtis, Whitham & McGinn

[57] ABSTRACT

A surgical saw blade for removable mounting in clamps having rectangular lugs and in clamps having circular pins, by way of closed slots having semi-circular distal ends, and arranged to have the respective centers of the semi-circular ends about a pattern radius. Each slot has a side face forming an included angle with a radial line from the hub center to the center of the slot semi-circular end. The included angle is alternating in rotational direction or, with a common offset about the pattern radius of the semi-circular ends, is in an identical direction for each slot.

3 Claims, 6 Drawing Sheets

UNIVERSAL SAW BLADE HUB

BACKGROUND OF THE INVENTION

1. Field of the Invention

The present invention relates to a power driven surgical saw blade. More particularly, the present invention relates to a surgical saw blade driven in an oscillating manner by a pneumatic or electrically powered actuator having a clamp for removably mounting the blade.

2. Background Description

Powered saws are frequently used for surgical procedures including orthopaedic surgery, and other operations requiring removal of bone material. There are several criteria that a surgical saw blade, the blade clamp, and blade drive should meet to enable a practical use. These criteria include a low blade weight, to minimize the oscillating mass, blade stiffness, resistance to metal-fatigue failure, a secure blade mount, ease of changing blades, ease of manufacture, since the blade is generally a single use item, and, to the extent possible, a single blade clamping and mounting mechanism.

The prior art includes a variety of cooperating blade, clamp and oscillating drive mechanisms which meet many of the above-identified criteria. For example, the blade and the corresponding clamp mechanism described in FIGS. 1–4 of U.S. Pat. No. 5,265,343, hereinafter referred to as "the '343 patent", provides, by the circular arrangement of round pins 5 and clamping faces 4 and 7, a secure mount for the blade 3 by way of the cooperating holes therein. One set of blades for use in a clamp such as described in the 343 patent is shown in FIGS. 5A through 5C of U.S. Pat. No. 5,306,285. Another blade, for use in a clamp similar to that of U.S. Pat. No. 5,265,343, is shown in FIG. 6A of U.S. Pat. No. 5,306,285.

Still another clamp mechanism, and its associated blade hub, is shown in U.S. Pat. Nos. 5,496,316 and 5,489,285, referenced collectively as "the '316 patent". The clamp described in the '316 patent is similar in function to the '343 clamp but uses rectangular lugs 20 instead of the '343 round pins 5. Otherwise, the '316's lugs 20 and the '343 pins 5 are both arranged in a circular pattern, both have clamping faces—the '343 surfaces 4 and 7, and the '316 surfaces 3 and 4, and both have means for biasing the blade against one clamping face—the '343 spring 22 and the '316 spring 7.

Another related art saw blade for use with a rectangular lug clamp, such as the '316 clamp, is shown in U.S. Design Pat. No. 343,247, referenced hereinafter as "the '247 patent." The blade hub shown in the '247 patent has radial slots formed to fit lugs, such as the '316 lugs 20, the slots being closed at both ends, thus differing in form from the '316 slots 35 which open to and communicate with the primary U-shaped slot.

Various commercial embodiments of the clamps described in the '343 and '316 patents are available. For example, the HALL VERSAPOWER®PLUS OSCILLA-TOR has a clamp substantially identical in structure, function, and operation as that shown in FIG. 1 of the '316 patent. The clamp shown in FIG. 1 of the '316 patent and the identified commercial product are referenced hereinafter collectively as "the '316-type clamp". The widely available HALL SERIES 3™ and HALL SERIES 4™ devices contain a clamp substantially identical in structure and function to that described in the '343 patent. Further, the MicroAire® Powermaster™ 7200 Oscillating Saw contains a clamp mounts blades interchangeably with that the '343 clamp. These identified commercial products and the corresponding clamp described in the '343 patent are referenced hereinafter, collectively, as "the '343-type clamp". Specific components of the '343-type clamp are referenced, where necessary, according to the item number in the '343 specification.

For proper operation with the '343-type clamp, the round holes formed in the blade hub 3 must have a fit precisely with the round locking pins 5. The reason is that radial motion to the blade 3 is imparted through the pins 5 and, accordingly, any clearance between the blade holes and the pins 5 will allow motion of the pins 5 within the hub holes, at the drive's oscillation rate. This may result in erratic blade motion, accelerated wear on the pins 5, and possible fatigue-related failure in the blade hub. Likewise, the lugs 20 of the '316 clamp must fit snug against the radial slots 35 of the blade. Accordingly, it can be seen that a saw blade hub formed to fit the round pins 5 of the '343 clamp will not have the elongated slots 35 required for the '316's rectangular lugs 20. Further, a saw blade having slots formed and dimensioned such as the '316 slots 35 will not fit properly with the '343's round pins 5 unless the lugs 20 were to have the same width as the round pins 5. Based on the present inventors' knowledge, however, of present commercial embodiments of clamps described in the '316 and '343 patents, the comparative diameter of the '343 type pins 5 and the '316 type lugs 20 does not allow a hub formed as FIG. 4 or FIG. 8 of the '316 patent to fit both the '343 and '316 type clamps.

One saw blade in the related art purportedly able to fit either a '343 type round pin clamp or a '316 type rectangular lug clamp is shown in FIG. 5 of the '316 patent. The '316 FIG. 5 blade achieves its purported objective by having enlarged circular openings 40 at the outer end of each of the slots 35, the holes 40 having a wider diameter than the width 37 of the slot.

However, the '316 FIG. 5 saw blade may have shortcomings. One shortcoming is that due to the slots 35 extending to and communicating with the primary U-shaped slot 33, along with the extent of the slot 35 and the wider circular openings 40, the '316 FIG. 5 hub is likely susceptible to breakage from metal fatigue at its flexure points.

For the foregoing reasons, there is a present need for an improved saw blade hub that will fit and operate reliably with both the '343 type round pins clamp and the '316 type rectangular lug clamp.

SUMMARY OF THE INVENTION

It is therefore an object of the present invention to provide a single saw blade hub which will securely and removably engage with a clamp having rectangular lugs and with a clamp having circular pins.

It is another object of the present invention to provide a saw blade hub which will be resistant to flex and resistant to fatigue-induced failures.

It is still another object of this invention to provide a saw blade hub which, by a novel arrangement of generally uniform diameter offset slots, will securely and reliably engage with both rectangular and round clamp pins.

These and other objects, aspects and advantages of the present invention will be more fully understood to one of ordinary skill from the detailed description hereinbelow.

DETAILED DESCRIPTION OF THE PREFERRED EMBODIMENTS

Figure 1:
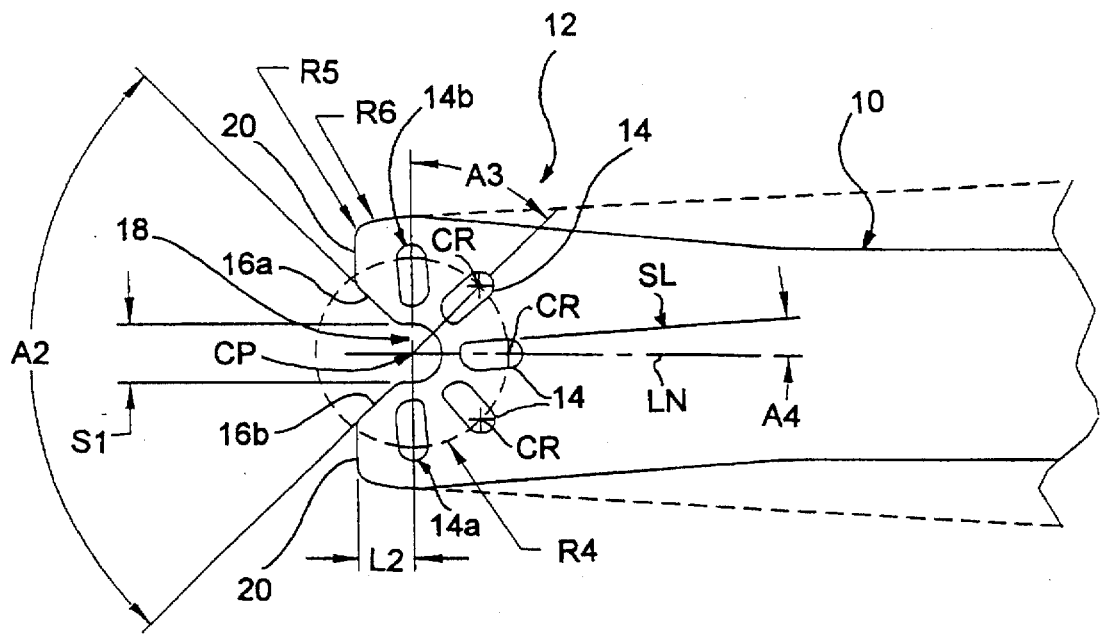
FIG. 1 is a planar view of a hub according to a first embodiment of the invention.
Figure 2:
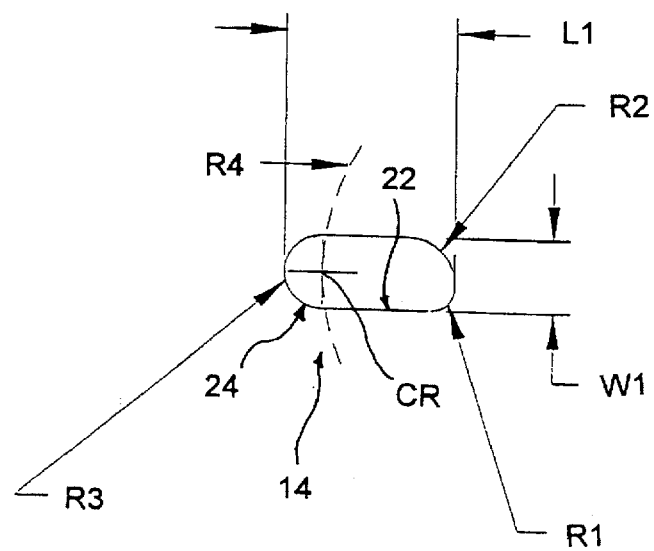
FIG. 2 is an enlarged view of one of the offset slots formed in the hub according to FIG. 1

Referring to FIGS. 1 and 2, this embodiment of the present invention includes a saw blade 10 having a hub portion 12 formed to include a plurality of, for this example, five offset slots 14, a V-shaped cut-out 16 having surfaces 16a and 16b, a U-shaped cutout 18 of width S1 formed around the center-point CP, and flats 20. The surfaces 16a and 16b are for engaging with rectangular lugs (not shown) of a '316-type clamp, and the included angle A2 is set to correspond to the lug dimensions of a particular clamp.

Each of the offset slots 14 has, for this example, a substantially uniform width W1, an extending face 22 and terminates at one end with a semi-circular end portion 24 and terminates at the other end with a radius R1 and R2. The semi-circular end 24 has a radius R3, which is substantially half the diameter W1 of the slot and which is centered at its respective center CR. Referring to FIG. 1, each of the slot's circular end center CR is arranged at a respective position on a circular pattern of radius R4, with one slot being on the longitudinal axis LN, referred to as the 3 o'clock position, and the others equally spaced by A3 degrees. The respective position of each of the centers CR, and the radius R4 of course correspond to the pin arrangement of the particular '343-type clamp(s)(not shown) for which the present blade is to be used.

The slots shown as 14a and 14b have centers CR that are located a distance L2 from the flats 20. The distance L2 is also set according to the particular '343-type clamp(s)(not shown) for which the present blade is to be used.

Referring to FIG. 1, each of the offset slots 14 has a face 22, extending in a direction that is angled, in a rotational direction alternating from slot 14 to slot 14, with respect to a line from the slot's semi-circular end center CR. The magnitude of the angle is shown as A4 degrees for the offset slot 14 at the 3 o'clock position, with SL being the direction of the face 24 and LN, the longitudinal axis, also being a line from that slot's circular end center CR to the center CP of the U-shaped cutout 18. The face 22 for each of the slots 14 alternates, as to which side of the slot 14 it is realized by, due to the alternating direction of the rotation A4. However, A4 is substantially the same magnitude for each of the slots 14, and therefore the A4 shown for the 3 o'clock slot is sufficiently representative.

Figure 3:
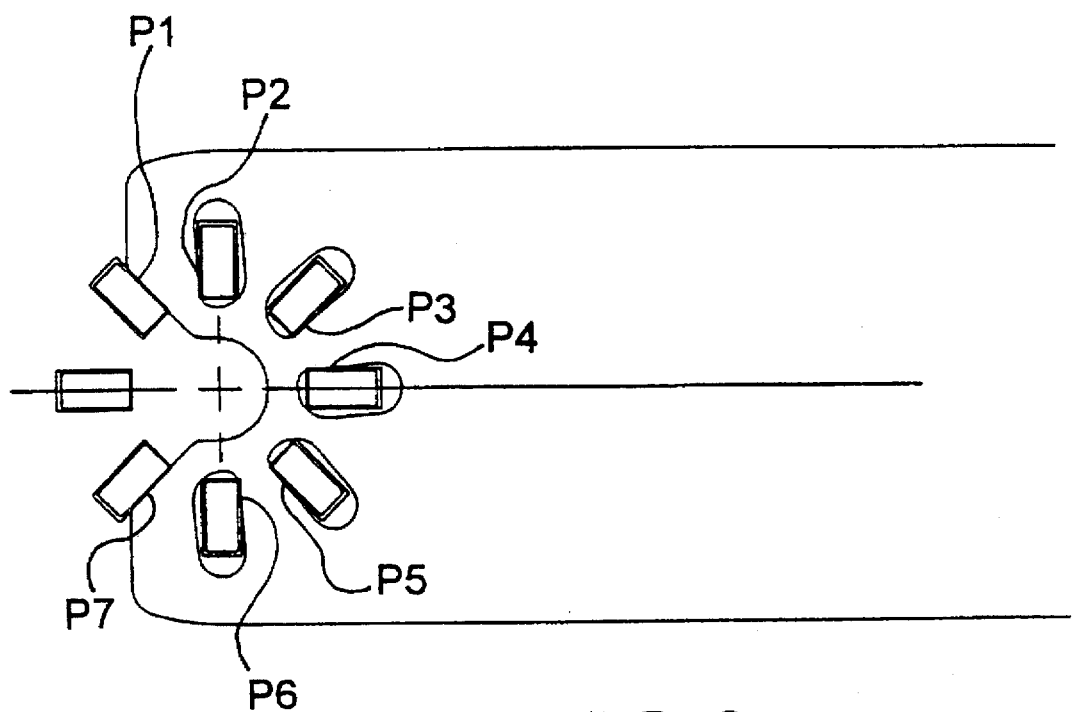
FIG. 3 is the hub according to FIG. 1 shown in cooperative engagement with a plurality of rectangular lugs of a first clamp.
Figure 4:
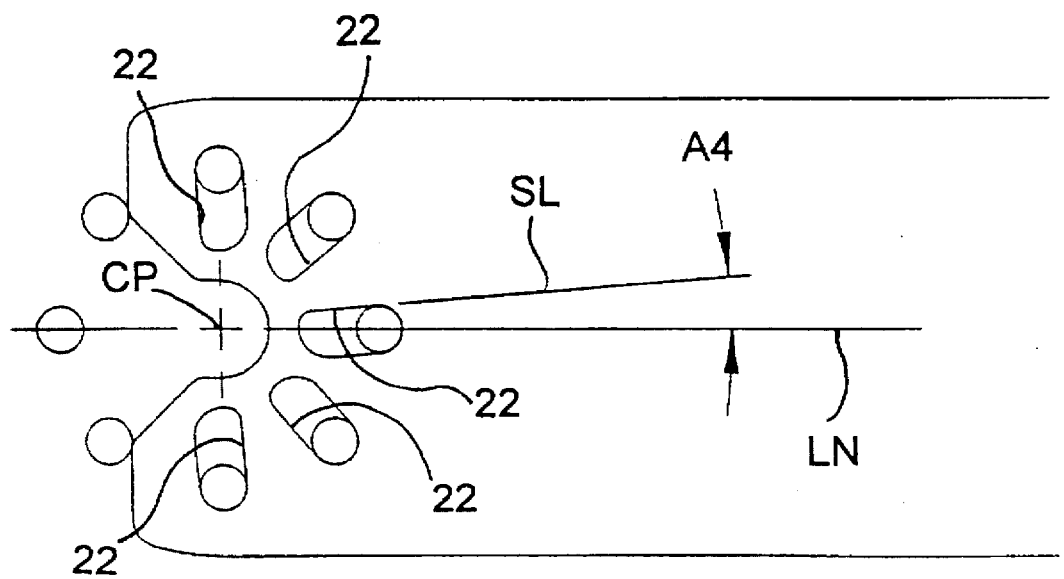
FIG. 4 is the hub according to FIG. 1 shown in cooperative engagement with a plurality of round pins of a second clamp.

Referring to FIGS. 3 and 4, the width W1 and the rotation arrangement of the slots 14 by A4, provides engagement of the hub 12 with an existing clamp's (not shown) rectangular lugs (not numbered), which are of the type shown as item 20 in the '316 patent and, as shown in FIG. 4, with circular pins (not numbered) associated with a clamp (not shown) of the type described, for example, in the '343 patent.

The width W1, and hence radius R3, corresponds to the diameter of the round pins of the specific '343-type clamp (s)(not shown) for which the present inventive blade is intended to be used. The rotation A4, length L1, and radii R1 and R2 is then set according to the width (not shown) and length (not shown) of the rectangular lugs of the particular '316-type clamp for which the blade is also intended. Referring, for example, to the '316 patent, the lugs shown therein as item 20 will generally have a bevel, shown therein as item 23. The bevel is shown as the region between the inner and outer rectangles (not numbered) in FIGS. 3,5 and 6. The dimensions of the bevel will of course factor into A4, length L1, and radii R1 and R2.

One method for ready selection of A4, L1, R1, and R2 is to overlay, by any generally available computer aided design ("CAD") tool, such as AUTOCAD®, the lug pattern and the pin pattern of the '316 and '343-type clamps for which the blade is intended as being used.

The blade 10 of this embodiment can be made of any of the materials generally known in the art of oscillating surgical saw blades, including 300 and 400 series stainless steel.

Figure 5:
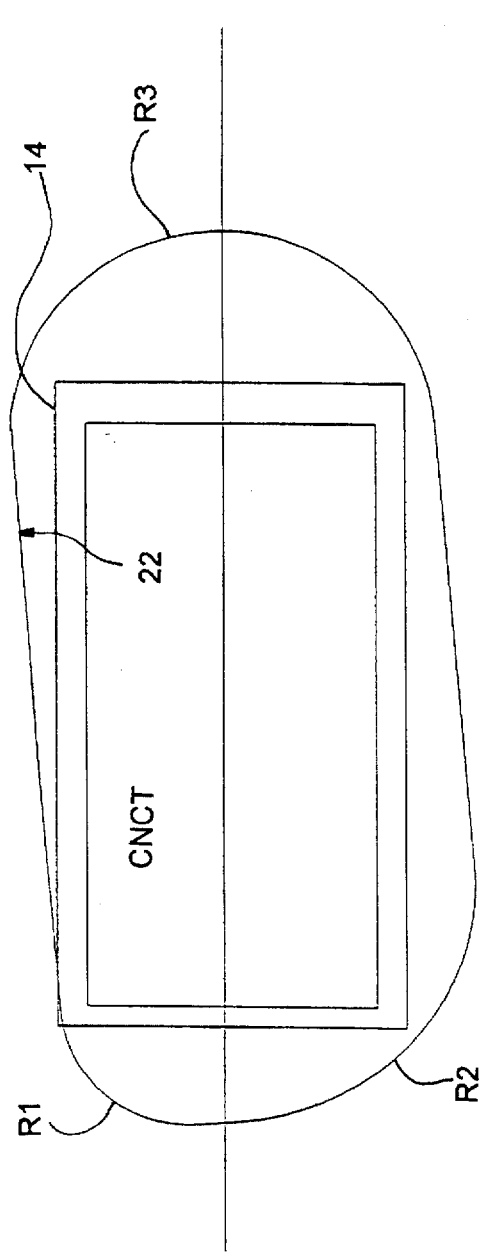
FIG. 5 is an enlarged view of one offset closed slot from FIG. 1 in cooperative engagement with a corresponding one rectangular lug.

Referring now to the present FIGS. 3 and 5, engagement of the present blade with rectangular lugs (not numbered) of the type shown as item 20 in the '316 patent is shown.

FIG. 3 shows contact in the region P1 surface 16a and the corresponding lug (not numbered), in the region P2 of the angled surface 22 of the slot 14 at the 12 o'clock position and the corresponding lug (not numbered), in the region P3 of the angled surface of the slot 14 at the 2 o'clock position and the corresponding lug (not numbered), at region P4 of the angled surface 22 of the slot 14 at the 3 o'clock position and the corresponding lug (not numbered), at region P5 of the angled surface 22 of the slot at the 5 o'clock position and the corresponding lug (not numbered), at region P6 of the angled surface 22 of the slot 14 at the 6 o'clock position and the corresponding lug (not numbered), and region P7 of the surface 16b and the corresponding lug (not numbered. FIG. 5 shows the contact region for each the slots 14 with its corresponding rectangular lug (not numbered) in representative form as CNCT.

As can be seen, the plurality of contact points P1 through P7 provides secure, stable engagement of the present blade with rectangular lugs (not numbered) formed and arranged as described in the '316 patent.

A specific example of this embodiment was built with the following nominal dimensions: L1=0.438", L2=0.185", W1=0.100, R1=0.030, R2=0.06, R4=0.670, A2=90 degrees, A3=45 degrees, and A4=3.2 degrees. Other dimensions, such as the blade 10 thickness (not shown), the blade 10 width (not numbered), the blade 10 length (not numbered), and the radius R5 and the radius R6 are known or are readily determined by one of ordinary skill. Further, the specific acceptable tolerances are both a matter of design choice and known or readily discernible to one of ordinary skill using standard design practices.

The example blade built according to these above-identified nominal dimensions tested to fit, and have the contact pattern shown in FIGS. 3–5 with, the following products: the HALL VERSAPOWER® PLUS OSCILLATOR, HALL SERIES 3™ and HALL SERIES 4™ and MicroAire Powermaster™ 7200 Oscillating Saw.

Figure 6:
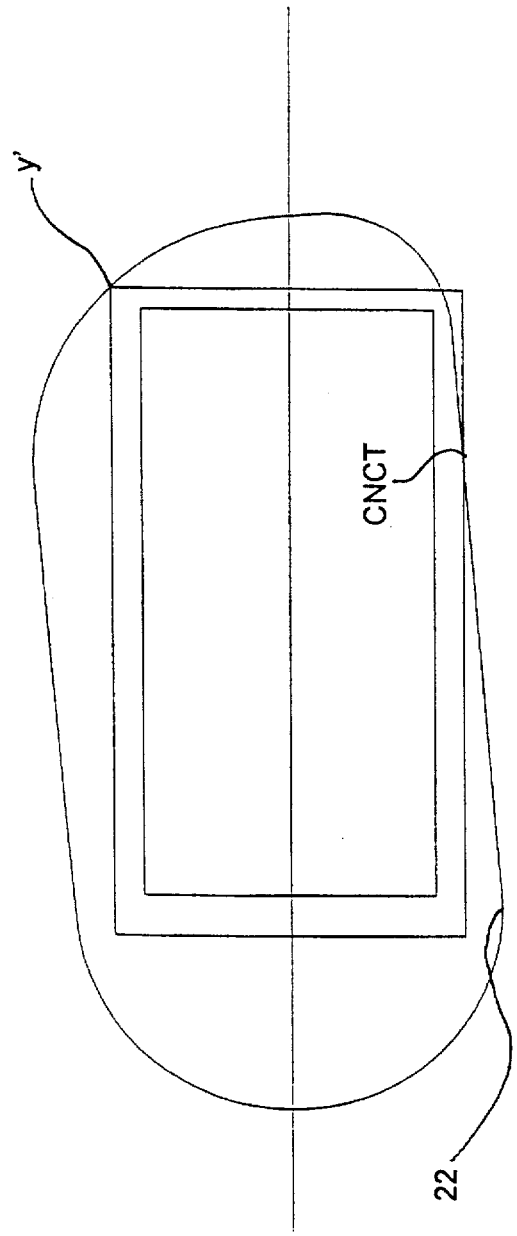
FIG. 6 is an enlarged view of a variation of FIG. 1, having a greater slot angle, showing the resulting cooperative engagement of one slot with a corresponding one rectangular lug.

A variation of the above-described embodiment is shown, in relevant part, in FIG. 6. More particularly, the A4 angle for the contact pattern shown in FIG. 5 was approximately 3.2 degrees. If the angle is increased, for example, to degrees then a contact pattern as shown in FIG. 6 can be obtained. Further, A4 can be selected to obtain a second contact point, which is at the point shown as Y1 on FIG. 6.

Figure 7:
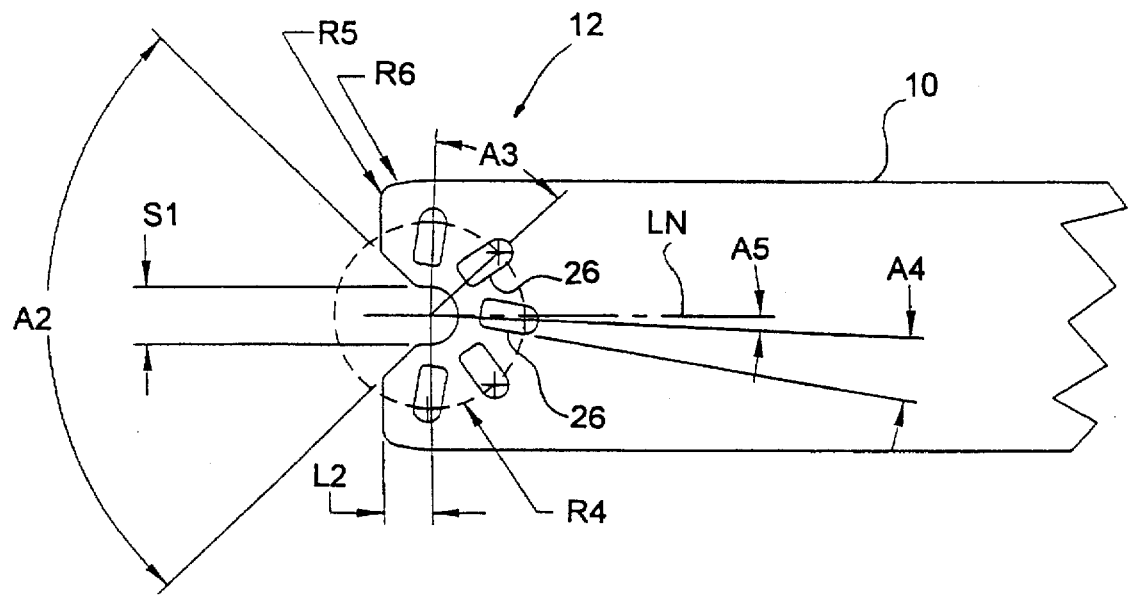
FIG. 7 is another embodiment of the present saw hub, having a variant in shape of the offset slots of FIG. 1.
Figure 8:
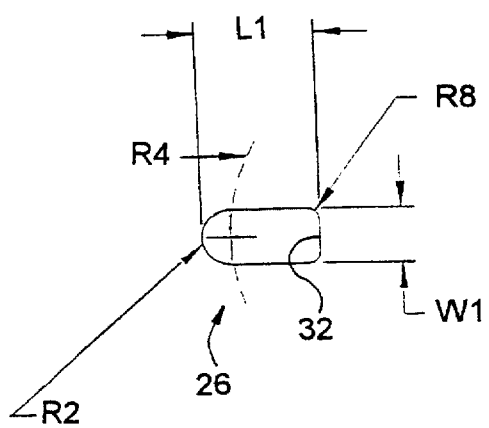
FIG. 8 is an enlarged view of one of the offset slots formed in the hub according to FIG. 7

Another embodiment of this invention is shown in FIGS. 7 and 8. This embodiment is similar to that described above, with offset slots 26 substituted for slots 14, each having one end formed as a semi-circle end 24, the same as the semi-circular end 24 of the slots 14, and a surface 30 extending similar to surface 22 of slots 14. However, each of the slots 26 is rotated in the same direction an angle A4 about the center of the slot's semi-circular end 24, instead of the alternating direction of rotation for A4 of the previous embodiment. Further, for this embodiment, the centers CR of each of the semi-semi-circular ends 24 are rotated, in unison, an angle A5 in the counterclockwise direction. Therefore, the semicircular end 24 appearing closest to the 12 o'clock position is actually A5 degrees counterclockwise and likewise for the semi-circular end 24 appearing closest to each of the 2, 3, 5, and 6 o'clock position. Further, the slots 26 each have a flat 32 with radii R8 instead of radii R1 and R2. The surface 30 is rotated an angle A4 with respect to a line from the center CR of the semi-circular end 24 to the center CP of the U-shaped cut-out 18.

Referring to FIGS. 7 and 8, the setting of the following: the pattern radius R4 of the semi-circular ends' centers CR, the length L2, the slot width S1, the included angle A2, and the angular spacing A3 is the same, and is selected on the same basis, as for the FIG. 1 embodiment.

Figure 9:
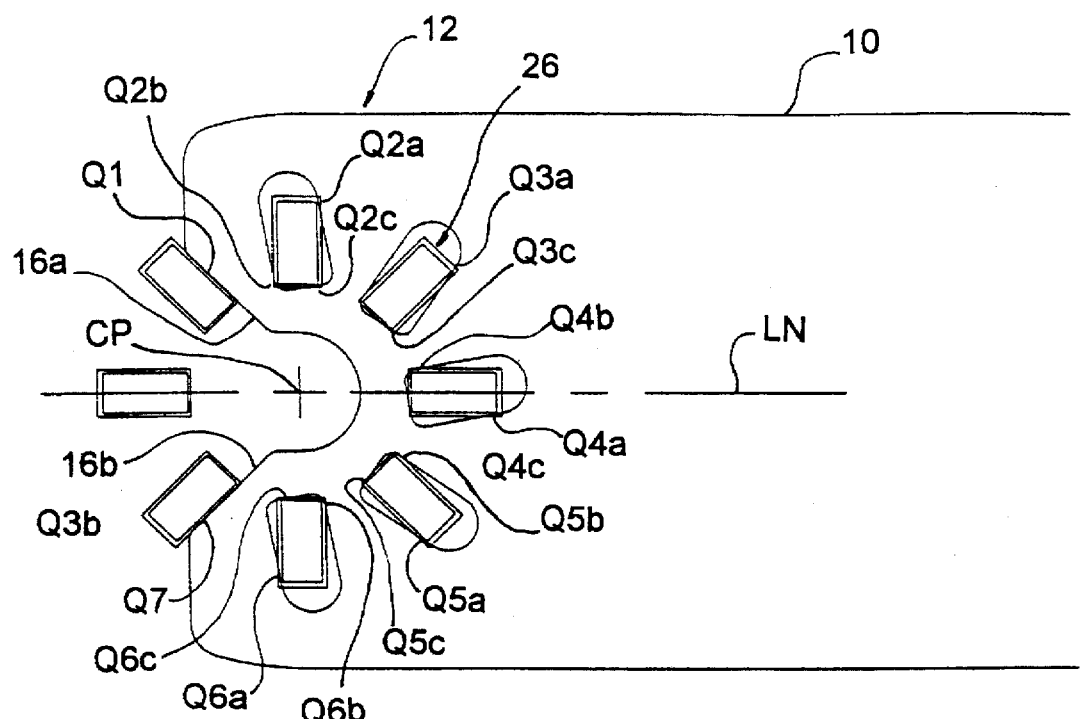
FIG. 9 is the hub according to FIG. 7 shown in cooperative engagement with a plurality of rectangular lugs of a first clamp.
Figure 10:
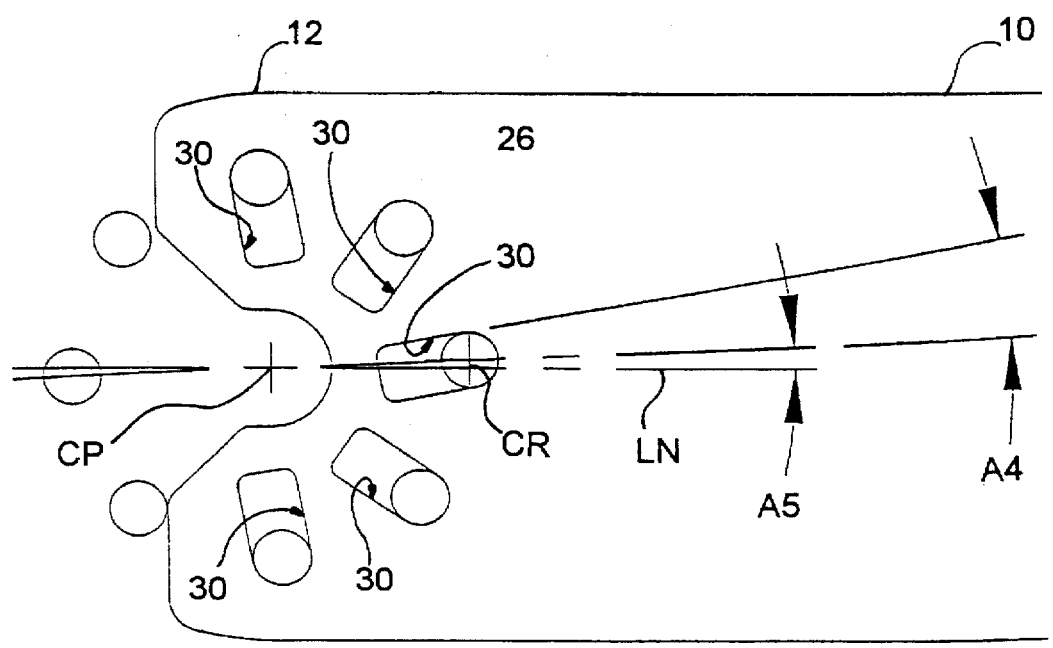
FIG. 10 is the hub according to FIG. 7 shown in cooperative engagement with a plurality of round pins of a second clamp.
Figure 11:
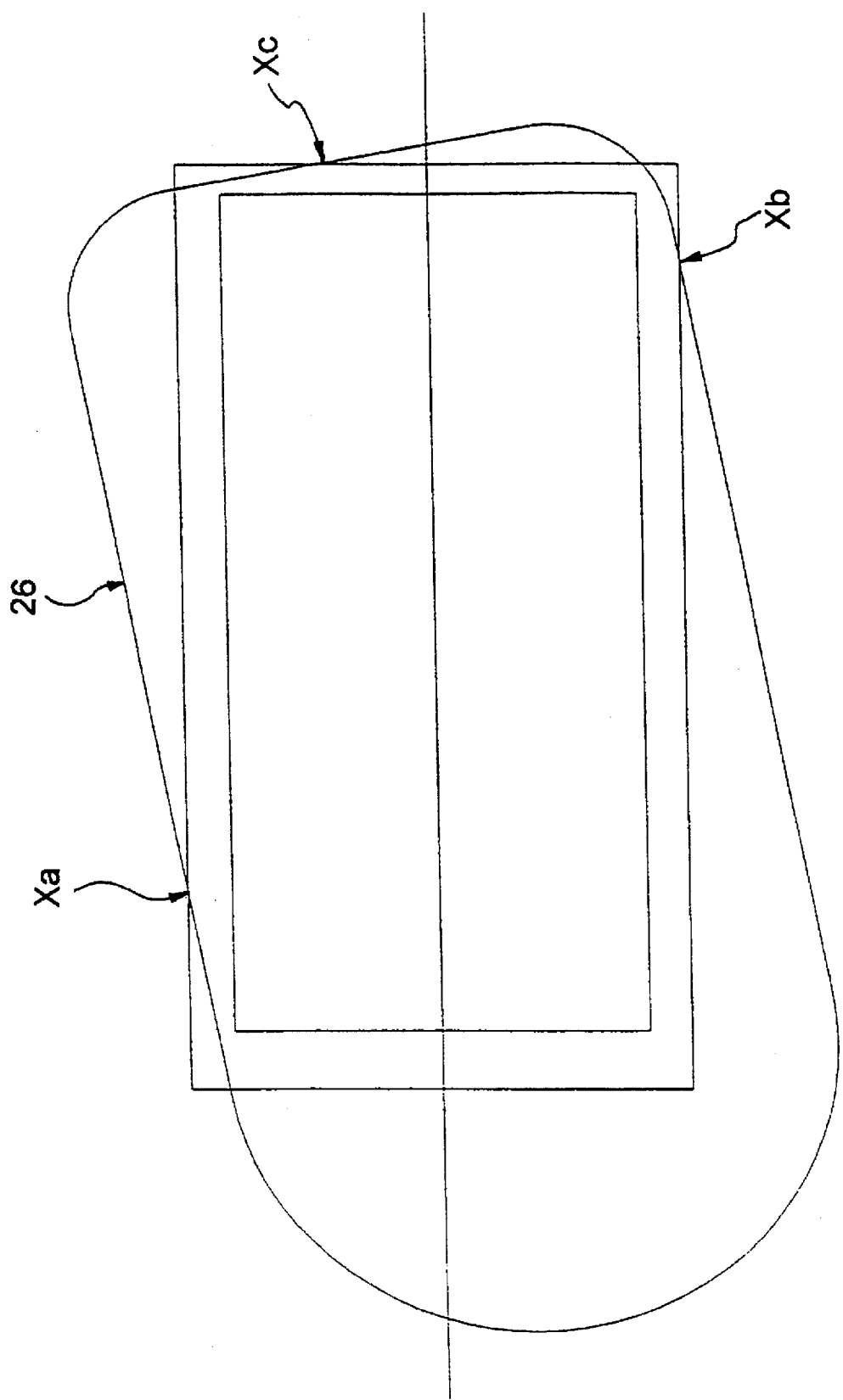
FIG. 11 is an enlarged view of one offset closed slot from FIG. 7 in cooperative engagement with a corresponding one rectangular lug.

However, the pattern rotation A5, the slot rotation angle A4, the width W1 and the length L1 are set in view of the lug contact pattern shown in FIGS. 9–11. These dimensions are easily set by overlaying, manually or by CAD, the lug pattern and the circular pin pattern of the '316 and '343-type clamps (not shown) that the blade is intended to be used with.

Referring now to FIGS. 9 and 11, the engagement pattern will be described. FIG. 9 shows contact at Q1 between a lug (not numbered) and surface 16a, at Q2a, Q2b and Q2c of slot 26 at the 12 o'clock position and the corresponding lug (not numbered), at Q3a, Q3b and Q3c of slot 26 at the 2 o'clock position and a corresponding lug (not numbered), at Q4a, Q4b and Q4c of slot 26 at the 3 o'clock position and the corresponding lug (not numbered), at Q5a, Q5b, and Q5c of the slot 26 at the 5 o'clock position and the corresponding lug (not numbered), at Q6a, Q6b and Q6c of the slot 26 at the 6 o'clock position and the corresponding lug (not numbered), and Q7 of surface 16b and its corresponding lug (not numbered).

FIG. 11 shows the three contact points for each the slots 26, in representative form, as Xa, Xb, and Xc.

As can readily seen, the plurality of contact points Q1 through Q7 effects secure, stable engagement of the present blade with rectangular lugs (not numbered) of a '316-type clamp. The slight rotational offset of the blade 10 when mounted in the '316-type clamp due to the angle A5 is negligible and has no detriment to the blade's function or operation.

The present invention has been described in reference to particular embodiments. As can be seen upon reading the present description, however, many alternative embodiments are realizable within the scope and meaning of the appended claims. For example, the U-shaped cut-out 18 of FIG. 1 could be formed as an octagonal cut-out. Another example relates to the radii R1 and R2 shown for FIG. 2. Other contours or segmented lines could be substituted for these radii to attain the contact pattern shown in either of FIGS. 5 or 6.

Having described our invention, what we claim is:

1. A saw blade for use in a first clamp and a second clamp, the first clamp having a plurality of rectangular lugs arranged in a pattern, and the second clamp having a plurality of round pins arranged in substantially the same pattern, said saw blade comprising:

a blade body having a longitudinal axis;

a cutting means disposed at a first end of said blade body;

a hub portion located at a second end of said blade body, said hub portion comprising a U-shaped cut-out formed around a hub center, said hub center being along said longitudinal axis, said U-shaped cut-out being closed at one end;

a plurality of slots, each of said slots having a first closed end and a second closed end, the second closed end being semi-circular and being centered around a respective center point, the second closed end being further distal from the hub center than the first closed end, the respective center points for each of the slots being along a radius centered at the hub center, each of said slots further including a side surface extending along a respective first line, said respective first line forming an included angle (A4) with respect to a line extending from the respective center point of the slot semi-circular end to the hub center, said included angle being greater than two degrees.

2. A saw blade according to claim 1, wherein at least one of said plurality of slots has said included angle in a first rotational direction and at least one of said plurality of slots has said included angle in a rotational direction opposite to said first rotational direction.

3. A saw blade according to claim 1, wherein a first slot from among said plurality of slots has a center point located at an offset angle (A5) in a first rotational direction from the longitudinal axis, a second slot from among said plurality of slots has a center point located at a rotational spacing angle (A3) in said first rotational direction from said first slot center point, and said rotational spacing angle is much greater than said included angle, a third slot from among said plurality of slots has a center point located at said rotational spacing angle in a direction opposite from said first rotational direction from said first slot center point, and each of the plurality of slots has said included angle in an identical rotational direction.

* * * * *